United States Patent [19]

Li

[11] Patent Number: 4,521,224

[45] Date of Patent: * Jun. 4, 1985

[54] SEMIPERMEABLE MEMBRANES PREPARED FROM POLYMERS CONTAINING PENDENT SULFONE GROUPS

[75] Inventor: George S. Li, Macedonia, Ohio

[73] Assignee: The Standard Oil Company, Cleveland, Ohio

[*] Notice: The portion of the term of this patent subsequent to Jan. 24, 2001 has been disclaimed.

[21] Appl. No.: 570,976

[22] Filed: Jan. 16, 1984

Related U.S. Application Data

[63] Continuation-in-part of Ser. No. 357,366, Mar. 12, 1982, Pat. No. 4,427,419.

[51] Int. Cl.³ .............................................. B01D 53/22
[52] U.S. Cl. .......................................... 55/16; 55/68; 55/158
[58] Field of Search ............................. 55/16, 68, 158; 210/500.2

[56] References Cited

U.S. PATENT DOCUMENTS

| | | | |
|---|---|---|---|
| 3,259,592 | 7/1966 | Fox et al. | 430/62 X |
| 3,534,528 | 10/1970 | Porter | 55/16 |
| 3,709,774 | 1/1973 | Kimura | 55/16 X |
| 3,735,559 | 5/1973 | Salemme | 55/16 |
| 3,994,860 | 11/1976 | Brousse | 210/500.2 X |
| 4,029,582 | 6/1977 | Ishii et al. | 55/16 X |
| 4,208,508 | 6/1980 | Hashino et al. | 210/500.2 X |
| 4,230,463 | 10/1980 | Henis et al. | 55/16 |
| 4,273,903 | 6/1981 | Rose | 210/500.2 X |
| 4,286,015 | 8/1981 | Yoshida et al. | 210/500.2 X |
| 4,351,860 | 9/1982 | Yoshida et al. | 210/500.2 X |
| 4,427,419 | 1/1984 | Li | 55/68 X |

Primary Examiner—Robert Spitzer
Attorney, Agent, or Firm—Gary R. Plotecher; Larry W. Evans

[57] ABSTRACT

Semipermeable membranes useful for the separation of gases from a mixture containing at least two fractions into enriched fractions of each, the membrane formed from at least one polymer containing a preponderance of arylene units of the formula

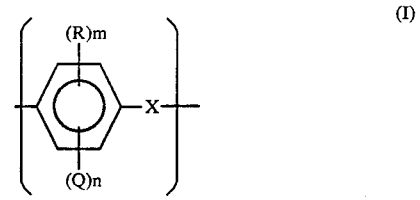

where each R is independently a $C_1$–$C_8$ aliphatic or a $C_5$–$C_7$ cycloaliphatic hydrocarbon radical, an aryl radical, an aralkyl radical or an alkaryl radical, each radical being free of a tertiary alpha-carbon atom; each Q is a radical of the formula

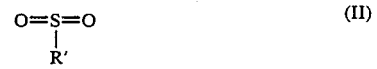

where R' is a $C_1$–$C_{20}$ linear or branched hydrocarbon or a nonpolymeric aryl radical; X is a divalent oxygen or sulfur atom or a carbonate group; m is an integer of 0–2; and n is 0–1 with the proviso that n is 1 in at least 10 percent of the arylene units of the polymer. A process is also provided whereby a mixture of gases is separated with the foregoing semipermeable membrane.

20 Claims, No Drawings

SEMIPERMEABLE MEMBRANES PREPARED FROM POLYMERS CONTAINING PENDENT SULFONE GROUPS

CROSS-REFERENCE TO RELATED APPLICATION

This is a continuation-in-part application of U.S. Ser. No. 357,366 filed Mar. 12, 1982, now U.S. Pat. No. 4,427,419.

TECHNICAL FIELD

This invention relates to semipermeable membranes. In one aspect, the invention relates to semipermeable membranes prepared from polymers containg pendent groups while in another aspect, the invention relates to the use of these membranes to separate various gaseous mixtures, such as carbon dioxide and methane, into enriched fractions of their constituent parts.

BACKGROUND ART

The art is replete with teachings describing various semipermeable membranes, their preparation and use. U.S. Pat. No. 3,350,844 teaches the enrichment of gases by permeation through a thin permeable film or membrane prepared from a polyarylene oxide film. U.S. Pat. No. 3,780,496 teaches the use of sulfonated polyxylene oxide membranes to separate helium, hydrogen and oxygen from gas mixtures.

While the membranes of the above teachings and others all display some level of utility, there exists a continuing search for new membranes and new applications for both new and known membranes. One application where the use of membrane technology may prove beneficial is in the separation of gaseous carbon dioxide-methane mixtures into enriched fractions of their constituent parts. Natural gas is generally found in combination with carbon dioxide. Removal of the carbon dioxide from the natural gas is desirable because it results in both a product (purified natural gas) of greater commercial worth and it provides purified carbon dioxide useful for other applications, such as enhanced oil recovery. Conventional separation processes generally employ cryogenic methods which are relatively energy intensive.

DISCLOSURE OF THE INVENTION

The subject of this invention is a semipermeable membrane useful for separating a gaseous mixture of carbon dioxide and methane into enriched fractions of each, the membrane formed from at least one polymer containing a preponderance of arylene units of the formula

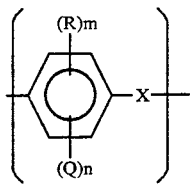

where each R is independently $C_1$–$C_8$ aliphatic or a $C_5$–$C_7$ cycloaliphatic hydrocarbon radical, an aryl radical, an aralkyl radical or an alkaryl radical, each radical being free of a tertiary alpha-carbon atom; each Q is a radical of the formula

where R' is a $C_1$–$C_{20}$ linear or branched hydrocarbon or a nonpolymeric aryl radical; X is a divalent oxygen or sulfur atom or a carbonate group; m is an integer of 0–2; and n is 0–1 with the proviso that n is 1 in at least 10 percent of the arylene units of the polymer. These membranes can be used in other applications, including reverse osmosis processes, and are easily prepared. Moreover, these membranes, demonstrate good durability.

A process is also provided for the separation of gases from a mixture containing at least two gases into two fractions, one fraction being enriched with at least one of the gases and the other fraction being depleted in same. The process is practiced by contacting the gaseous mixture with a semipermeable membrane in such a manner that a portion of the gaseous mixture selectively passes through the membrane resulting in the enriched fraction being on one side of the membrane and the depleted fraction being on the other side of the membrane, the improvement comprising the use of a semipermeable membrane formed from at least one polymer containing a preponderance of arylene units of the formula

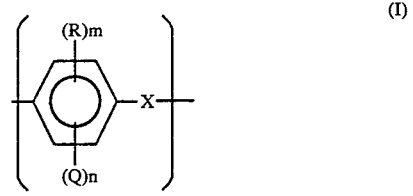

as described in the preceding paragraph.

PREFERRED MODE FOR CARRYING OUT THE INVENTION

The membrane of this invention is prepared from at least one polymer containing a preponderance of arylene units of formula I. As here used, the term "preponderance" means that at least 50%, preferably at least 55%, of the units of the polymer are arylene units of formula I. In those polymers where the arylene units comprise less than essentially 100% of the total units of the polymer, the other units can be of essentially any structure that does not prevent the polymer from being fabricated into a membrane useful for separating a gaseous mixture of carbon dioxide and methane to enriched fractions of each.

These other units can be incorporated into the polymer to serve simply as a diluent to the arylene units or to impart specific properties to the polymer which will eventually be manifested in the membrane, properties such as tensile strength, hydrophilicity, hydrophobicity and the like. These other units must also be able to polymerize with the arylene units in a manner sufficient to allow formation of polymers of adequate molecular weight, e.g., at least about 20,000 weight average molecular weight. These other units include monomers that polymerize through an ethylenically unsaturated bond, as ethylene, styrene and the like, a hydroxy group, such as diethylene glycol; an amine group, such as ethylene diamine; and so forth. Preferably, polymers employed to form the membranes of this invention contain no significant amount of structural units other than the arylene units of formula I, i.e., polymers consisting essentially of arylene units of formula I.

As noted above, X can be divalent oxygen, —O—, divalent sulfur, —S—, or a carbonate group

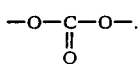

As the term "independently" implies, the definition of X can vary from arylene unit to arylene unit and thus a polymer consisting essentially of arylene units of formula I can contain all three linkages although preferably the X linkage has the same definition throughout the polymer, i.e., all carbonate, all oxygen or all sulfur. Divalent oxygen is the preferred definition of X.

Typical groups represented by R in formula I include methyl, ethyl, propyl, hexyl, cyclohexyl, cyclohexenyl, phenyl, tolyl, xylenyl, phenethyl, and the like. If desired, R can contain inert substituents, i.e., substituents that are nonreactive with the components of the permeant under separation conditions, although preferably R is free of any such substituents. If R is present (m is 1 or 2) then preferably it is dependently a $C_1$–$C_4$ alkyl radical, most preferably a methyl radical. When m is 0, R is not present.

R′ in the definition of Q can be any linear or branched hydrocarbon having from one to about 20 carbon atoms including saturated compounds such as methyl, ethyl, propyl, butyl, t-butyl, octyl, hexadecyl and the like, as well as unsaturated, e.g., alkenes, alkynes and the like. Polyarylenes containing such Q groups can be prepared by a Friedel-Crafts synthesis by reacting the arylene monomer with an alkylsulfonyl halide under suitable conditions and with a catalyst.

R′ can also be any nonpolymeric aryl radical, such as phenyl, tolyl, xylenyl and phenethyl. By nonpolymeric is meant that the aryl radical is not part of a polymer chain, i.e., the aryl radical of an arylene unit of another polymer strand of formula I or in other words, the sulfone group, O=S=O, does not link two independent polymer strands. However, the aryl radical here includes multi-ring compounds such as biphenyl, naphthyl, diphenyloxide, etc. Preferred such aryl radicals are phenyl, tolyl, xylenyl and phenethyl.

Of the total number of arylene units formula I in any given polymer, at least 10% of those arylene units contain the substituent Q (n is 1). Preferably, at least 20% of the arylene units of the polymer contain Q and most preferably, at least 30%. These percent figures assume a polymer consisting essentially of arylene units of formula I and thus the percent of arylene units containing Q and those polymers containing structural units other than those of formula I should be increased accordingly. For example, if 75% of the structural units of the polymer are formula I, then the minimal number of arylene units containing Q should be at least 30% higher than in a comparable polymer of essentially 100% arylene units.

R′ is preferably an aryl radical of the formula

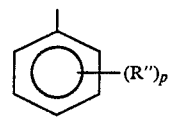

where each R″ is independently a $C_1$–$C_6$ aliphatic radical, and p is an integer of 0–4. If p is a positive integer (greater than 0), preferably it is 1 or 2 and then R″ is preferably a $C_1$–$C_3$ alkyl radical.

In a preferred embodiment of this invention, the semipermeable membrane is prepared from a polyphenylene ether having a repeating structural unit of formula I where X is divalent oxygen and m and n are 0. The weight average molecular weight of this material is typically at least about 20,000 and preferably at least about 50,000. The maximum weight average molecular weight is limited only by practical considerations, particularly the film-forming ability of the polymer, but typically it does not exceed about 1,000,000 weight average molecular weight. These polymers and their preparation are defined at length in the above-referenced U.S. Pat. No. 3,350,844, the subject matter of which is incorporated herein by reference.

The polyphenylene oxide polymer described hereinabove can be readily converted to a polymer having a repeating structural unit of formula I where X is oxygen and R′ is a nonpolymeric aryl radical by contacting the polymer with chlorosulfonic acid as the sulfonating agent. This will sulfonate the benzene nucleus of the arylene unit, the sulfur being present in either a sulfonic acid group, —$SO_3H$, or in a sulfonyl chloride group, —$SO_2Cl$. This procedure is defined in greater detail by U.S. Pat. No. 3,259,592 (except polyxylene oxide is used in lieu of polyphenylene oxide) the teachings of which are incorporated herein by reference.

The sulfonated polyphenylene oxide is then converted to a polyphenylene oxide containing Q groups by contacting the sulfonated resin with an aromatic compound, such as benzene, toluene, xylene, and/or ethylbenzene. The temperature and pressure at which this second step can be performed can vary widely but is typically conducted at a temperature between about 100° and about 150° C. and preferably between about 110° and about 140° C. The pressure at which this reaction takes place can vary from sub- to superatmospheric pressure. Generally, an amount in excess of stoichiometric requirements of the aromatic compound is employed to insure complete reaction of all available sulfonic acid and/or sulfonyl chloride groups.

The polymers of this invention can also be prepared by other methods such as reacting a polyphenylene oxide polymer containing halogen with a salt of an aromatic sulfonic acid or reacting a polymer containing some anion, such as lithium, with a chlorosulfonyl aromatic. However, the method described in the preceding paragraph is generally preferred due to its relative convenience. The reactions of this preferred method are typically conducted in the presence of a suitable solvent, such as chloroform.

In order to prepare a polymer having a repeating structural unit of formula I where X is oxygen and R′ is a linear or branched hydrocarbon, a Friedel-Crafts synthesis is employed. The reaction takes place by contacting a solution of polyphenylene oxide with alkylsulfonyl halides, e.g., bromides, chlorides, fluorides in the presence of a Lewis acid (AlCl$_3$, SnCl$_4$ and the like). Halogenated solvents or polar solvents, particularly nitrobenzene are employed for the reaction. Typical reaction temperatures range between 0° and 100° C.; typical reaction times are from a few hours to 16 hours. Reaction mixtures are usually purged with nitrogen to aid in the removal of hydrogen halide by-products.

The semipermeable membrane can be manufactured by any conventional method. In one embodiment, the polymer is dissolved in a suitable solvent to form about a five to about a 20, preferably a seven to about a 15, weight percent solution. Generally any polar solvent can be employed with chloroform, dimethylformamide, dimethylsulfoxide, dimethylacetamide, acetone and methylethyl ketone being exemplary. The solution is then poured over a clean glass plate and spread evenly due to a uniform thickness with the aid of a doctor blade. The membranes are then air dried, removed from the glass plate and further dried in air under ambient conditions for a suitable period of time, generally in excess of 24 hours. In other embodiments, these membranes can be manufactured by the various laboratory and commercial techniques known in the art. These membranes can also be manufactured in structures other than films, such as hollow fibers.

The membranes of this invention can be cast at any desirable thickness although membranes having a thickness between 25 mils (1 mil equals 25 micrometers) and 1,000 angstroms, preferably between 10 mils and 1,000 angstroms. These membranes demonstrate good permeability, durability, flexibility, strength and corrosion resistance.

The process of this invention is suitable for separating any one of a number of different gases such as hydrogen, helium, nitrogen, oxygen, carbon monoxide, carbon dioxide, hydrogen sulfide, ammonia, water (vapor) and C$_1$ to C$_4$ hydrocarbons from mixtures containing the same. Typical gas mixtures where separation is desirable include H$_2$/N$_2$; H$_2$/CO; H$_2$/C$_1$ to C$_4$; H$_2$/O$_2$; H$_2$/NH$_3$; CO$_2$/C$_1$ to C$_4$; CO$_2$/N$_2$; H$_2$S/C$_1$ to C$_4$; O$_2$/N$_2$; N$_2$/NH$_3$/ He/C$_1$ to C$_4$; H$_2$S/C$_1$ to C$_4$ and H$_2$O/C$_1$ to C$_4$. The membrane can also be employed for the separation of mixtures comprising three gases or more. It is to be understood that not all gas pairs or mixtures will be separated optimally over a given membrane of the present invention. So long as the membrane exhibits a selectivity for at least one gas in a mixture, it has utility for that particular mixture. The semipermeable membranes of this invention find particular utility for the separation of gaseous carbon dioxide-methane mixtures into their constituent parts, i.e., enriched fractions of carbon dioxide and methane.

These membranes are also useful for separating liquid mixtures, such as ethanol-water, water-aldehyde, salt water, carboxylic acid-water and the like. If used to separate liquid mixtures into their constituent parts, then these membranes are used in the same manner as known membranes for these separations. Furthermore, these membranes can be used in any one of a number of different manners including reverse osmosis and pervaporation, the latter being a combination of permeation and evaporation.

The following examples are illustrative of specific embodiments to this invention and unless indicated to the contrary, all parts and percentages are by weight.

SPECIFIC EMBODIMENTS

Polymer Preparation

The polymers employed herein to manufacture the membranes were all based upon dimethyl polyphenylene oxide, hereinafter polyphenylene oxide, having a weight average molecular weight of about 46,000. One typical preparation of the polymer commenced with contacting dimethyl polyphenylene oxide dissolved in chloroform with a stoichiometric excess of chlorosulfonic acid, also dissolved in chloroform. Chlorosulfonated-polyphenylene oxide precipitated from the chloroform, was recovered and then further reacted at an elevated temperature (typically about 120° C.) with an aromatic compound, such as benzene, toluene, etc. The final dark solution was then cooled, precipitated with methanol, washed with dilute sodium bicarbonate and dried.

Membrane Preparation

All the membranes tested herein were prepared from the arylsulfonated polyphenylene oxide polymers prepared by the foregoing descriptions. The membranes were prepared by mixing a dilute (about 5 to about 20 weight percent) solution of polymer in a suitable solvent, typically about 7 weight percent poured over a clean glass plate and spread evenly to a uniform thickness with the aid of a doctor blade, air dried, removed from the glass plate, and further dried in air at ambient conditions for at least 24 hours.

Apparatus and Procedure

A modified Gilbert cell was used to test the permeation of the films. The test side was exposed to a carbon dioxide/methane/nitrogen mixture in a mole ratio of 2.99:32:65. The permeant was picked up by a carrier gas, helium, and injected intermittently through a sample valve into a GC column for analysis. The experiments were conducted at 23° C., the partial pressure of the test gas on the feed side was 29.7 psi (0.21 MPa) and the partial pressure of the product gas on the permeant side was about 0 and purged with 29.77 psi (0.21 MPa) helium at a flow rate much in excess of the permeation rate. The area of the test membrane was 45.8 square cm. The film thickness was about 1-2 mils.

The carbon dioxide permeability and carbon dioxide/methane selectivity figures are reported in Table I. The sulfur content of the modified polymers from which the membrane was formed is given in weight percent and the organic portion of the sulfone group, i.e., R′, is listed separately.

TABLE I

| Ex. No. | R′ | Sulfur Content (WT %) | Selectivity CO$_2$/CH$_4$ | $\overline{P}$CO$_2$ |
|---|---|---|---|---|
| 1 | Tolyl | 7 | 24 | 121 |
| 2 | m-Xylenyl | 2.5 | 22 | 99 |
| 3 | Phenyl | 4.7 | 21 | 135 |
| 4 | Ethylbenzyl | 2.8 | 18 | 100 |
| A* | None | 0 | 18 | 87 |
| B** | None | — | 37 | 27 |

*Membrane prepared from unmodified polyphenylene oxide
**Membrane prepared from polyphenylene oxide, sulfur content not measured Selectivity, as is known, is a comparison of the permeability, $\overline{P}$, of one gas divided by the permeability of the second gas in the mixture. Normally, the less permeable member of the gas pair is placed in the denominator and the selectivity factor will be a number greater than one. Permeability, in turn, is customarily calculated according to the relationship $$\overline{P} = \frac{(cc)(cm)}{(sec)(cm^2)(cmHg)}$$

where cc is the volume of the permeating gas at standard temperature and pressure, cm is the thickness of the membrane, sec is the time in seconds for a given amount of gas to be permeated, cm² is the area of the membrane and cmHg is the pressure differential over the membrane in cm of mercury. Permeability as such as reported in Barrers, one Barrer being equal to $1 \times 10^{-10} \overline{P}$. Gas pressures on the membranes of this invention can range from about 0.10 to 200 Mpa with five to 100 MPa being preferred.

The above data clearly demonstrates the general superiority of membranes formed from aryl sulfonated polypropylene oxide polymers. The membrane formed from the toluene sulfonated polypropylene oxide polymer was ⅔ better than the membrane prepared from unmodified polypropylene oxide in both carbon dioxide permeability and selectivity. Membranes formed from these modified polypropylene oxide polymers have also been shown to be essentially impervious to boiling water while membranes formed from sulfonated polypropylene oxide are generally water swellable.

As stated herein, R' in the sulfonyl group Q can also be non-aromatic, i.e., $C_1$–$C_{20}$ linear or branched hydrocarbon. By way of example, where R' in the sulfonyl group Q is hexadecyl a different procedure was followed which commenced by contacting polyphenylene oxide in nitrobenzene (5 percent solution) in the presence of $AlCl_3$. To this mixture was added 1-hexadecanesulfonyl chloride while nitrogen gas was bubbled therethrough. After a reaction time of six hours at 40° C., the mixture was washed with water, dried on anhydrous $MgSO_4$, filtered and precipitated from methanol.

A membrane was then prepared as described hereinabove and employed for the separation of the $CO_2/CH_4$ mixture (2.99/32/65). For comparison, a membrane was also again prepared from an unmodified polyphenylene oxide, Selectivity $CO_2/CH_4$ for the hexadecyl sulfonated polyphenylene oxide membrane was equivalent to the unmodified polymer membrane while $\overline{P}CO_2$ was approximately 20 percent higher, thereby demonstrating the improvement when the membrane comprises a sulfonated polymer.

While this invention has been described in specific detail by the preceding examples, this detail is provided for the purpose of illustration only and is not to be construed as limitations upon the invention as described in the following claims.

I claim:

1. A semipermeable membrane useful for the separation of gases from a mixture containing at least two fractions into enriched fractions of each, the membrane formed from at least one polymer containing a preponderance of arylene units of the formula

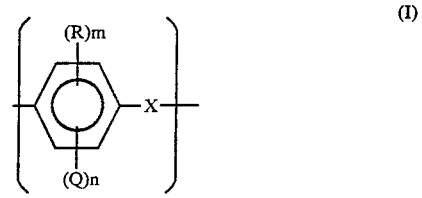

where
each R is independently a $C_1$–$C_8$ aliphatic or a $C_5$–$C_7$ cycloaliphatic hydrocarbon radical, an aryl radical, an aralkyl radical or an alkaryl radical, each radical being free of a tertiary alpha-carbon atom;
each Q is a radical of the formula

where R' is a $C_1$–$C_{20}$ linear or branched hydrocarbon;
X is a divalent oxygen or sulfur atom or a carbonate group;
m is an integer of 0–2; and
n is 0–1 with the proviso that n is 1 in at least 10 percent of the arylene units of the polymer.

2. The membrane of claim 1 where R' is hexadecyl.

3. The membrane of claim 2 where n=1 in at least 20 percent of the arylene units of the polymer.

4. The membrane of claim 3 where X is a divalent oxygen atom.

5. The membrane of claim 4 where each R is independently a $C_1$–$C_4$ alkyl radical.

6. The membrane of claim 4 where m is 2.

7. The membrane of claim 6 where at least one of the polymers used to form the membrane consists essentially of repeating units of I.

8. The membrane of claim 7 formed from essentially only the polymer consisting essentially of repeating units of I.

9. The membrane of claim 1 wherein the gases in said mixture are selected from the group consisting of hydrogen, helium, oxygen, nitrogen, carbon monoxide, carbon dioxide, hydrogen sulfide, ammonia, water vapor and $C_1$ to $C_4$ hydrocarbons.

10. A membrane of claim 9 wherein said mixture of gases comprises carbon dioxide and methane.

11. In a process for the separation of gases from a mixture containing at least two gases into two fractions, one fraction being enriched with at least one of said gases and the other fraction being depleted in same, the process comprising:

contacting the gaseous mixture with a semipermeable membrane in such a manner that a portion of the gaseous mixture selectively passes through the membrane resulting in the enriched fraction being on one side of the membrane and the depleted fraction being on the other side of the membrane, the improvement comprising the use of a semipermeable membrane formed from at least one polymer containing a preponderance of arylene units of the formula

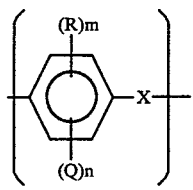

where
each R is independently a $C_1$–$C_8$ aliphatic or a $C_5$–$C_7$ cycloaliphatic hydrocarbon radical, an aryl radical, an aralkyl radical or an alkaryl radical, each radical being free of a tertiary alpha-carbon atom;
each Q is a radical of the formula

where R' is a $C_1$–$C_{20}$ linear or branched hydrocarbon;

X is a divalent oxygen or sulfur atom or a carbonate group;
m is an integer of 0–2; and
n is 0–1 with the proviso that n is 1 in at least 10 percent of the arylene units of the polymer.

12. The process of claim 11 where R' is hexadecyl.

13. The process of claim 12 where n=1 in at least 20 percent of the arylene units of the polymer.

14. The process of claim 13 where X is a divalent oxygen atom.

15. The process of claim 14 where each R is independently a $C_1$–$C_4$ alkyl radical.

16. The process of claim 14 where m is 2.

17. The process of claim 16 where at least one of the polymers used to form the membrane consists essentially of repeating units of I.

18. The process of claim 17 formed from essentially only the polymer consisting essentially of repeating units of I.

19. The process of claim 11 wherein the gases in said mixture are selected from the group consisting of hydrogen, helium, oxygen, nitrogen, carbon monoxide, carbon dioxide, hydrogen sulfide, ammonia, water vapor and $C_1$ to $C_4$ hydrocarbons.

20. The process of claim 19 wherein said mixture of gases comprises carbon dioxide and methane.

* * * * *